(12) United States Patent
Honda

(10) Patent No.: US 11,182,897 B2
(45) Date of Patent: Nov. 23, 2021

(54) MEDICAL IMAGE PROCESSING DEVICE, MEDICAL OBSERVATION DEVICE, MEDICAL OBSERVATION SYSTEM, OPERATION METHOD IN MEDICAL IMAGE PROCESSING DEVICE, AND COMPUTER-READABLE RECORDING MEDIUM

(71) Applicant: Sony Olympus Medical Solutions Inc., Tokyo (JP)

(72) Inventor: Takeshi Honda, Kanagawa (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 16/776,534

(22) Filed: Jan. 30, 2020

(65) Prior Publication Data

US 2020/0302599 A1   Sep. 24, 2020

(30) Foreign Application Priority Data

Mar. 22, 2019   (JP) .............................. JP2019-055723

(51) Int. Cl.
| | |
|---|---|
| *G06T 7/00* | (2017.01) |
| *G06T 7/70* | (2017.01) |
| *A61B 10/02* | (2006.01) |
| *G02B 21/00* | (2006.01) |
| *G02B 21/36* | (2006.01) |
| *A61B 90/00* | (2016.01) |
| *A61B 5/00* | (2006.01) |
| *A61B 90/25* | (2016.01) |

(52) U.S. Cl.
CPC ............ *G06T 7/0012* (2013.01); *A61B 10/02* (2013.01); *G02B 21/0012* (2013.01); *G02B 21/367* (2013.01); *G06T 7/70* (2017.01); *A61B 5/0077* (2013.01); *A61B 90/25* (2016.02); *A61B 2090/373* (2016.02); *G06T 2207/10056* (2013.01); *G06T 2207/30096* (2013.01)

(58) Field of Classification Search
CPC ..................... G06T 7/0012; G06T 7/70; G06T 2207/10056; G06T 2207/30096; G02B 21/367; G02B 21/0012; A61B 10/02; A61B 2090/373; A61B 90/25; A61B 5/007

See application file for complete search history.

(56) References Cited

U.S. PATENT DOCUMENTS

| | | | | |
|---|---|---|---|---|
| 2011/0249910 | A1* | 10/2011 | Henderson | G06K 9/00134 382/278 |
| 2013/0182901 | A1* | 7/2013 | Ishida | G06T 7/344 382/103 |

(Continued)

FOREIGN PATENT DOCUMENTS

JP   2016-202726 A   12/2016

*Primary Examiner* — Tracy Y. Li
(74) *Attorney, Agent, or Firm* — Xsensus, LLP

(57) ABSTRACT

A medical image processing device includes circuitry configured to: calculate relative information including relative positional relation of a pathologically diagnosed position in a subject with respect to an observation image of the subject captured by an imager, by using data on the observation image and pathological diagnosis information on the subject; and generate, based on the relative information, data on a displayed observation image resulting from addition of the pathological diagnosis information to the data on the observation image.

12 Claims, 8 Drawing Sheets

(56) References Cited

U.S. PATENT DOCUMENTS

2013/0188851 A1* 7/2013 Miyasa ................ G06T 7/0012
382/131
2015/0347505 A1* 12/2015 Ohashi ................ G06F 16/245
707/754
2016/0300351 A1* 10/2016 Gazit ...................... G06T 7/187

* cited by examiner

MEDICAL IMAGE PROCESSING DEVICE, MEDICAL OBSERVATION DEVICE, MEDICAL OBSERVATION SYSTEM, OPERATION METHOD IN MEDICAL IMAGE PROCESSING DEVICE, AND COMPUTER-READABLE RECORDING MEDIUM

This application claims priority from Japanese Application No. 2019-055723, filed on Mar. 22, 2019, the contents of which are incorporated by reference herein in its entirety.

BACKGROUND

The present disclosure relates to a medical image processing device, a medical observation device, a medical observation system, an operation method in the medical image processing device, and a computer-readable recording medium.

In surgery aimed at resection or extirpation of lesions, there is a demand for lesions including margins to be resected or extirpated for minimization of the risk of recurrence of the lesions. However, for minimization of the risk of complication and preservation of the functions, resection and extirpation need to be kept to a minimum, and there is thus a demand for accurate identification of resection lines.

For example, known in neurosurgical microsurgery is a technique for: identification of a tumor by fluorescence observation through use of an agent, such as 5-ALA or fluorescein; and ascertainment of a resection line (as seen in, for example, Japanese Laid-open Patent Publication No. 2016-202726).

SUMMARY

According to the above cited technique, results of observation are displayed on a separate monitor and it has thus been difficult to say that a doctor is able to easily identify the position and area of a lesion in an observation image during surgery.

There is a need for a medical image processing device, a medical observation device, a medical observation system, an operation method in the medical image processing device, and a computer-readable recording medium, which enable a doctor to easily identify the position and area of a lesion in an observation image during surgery.

According to one aspect of the present disclosure, there is provided a medical image processing device including circuitry configured to: calculate relative information including relative positional relation of a pathologically diagnosed position in a subject with respect to an observation image of the subject captured by an imager, by using data on the observation image and pathological diagnosis information on the subject; and generate, based on the relative information, data on a displayed observation image resulting from addition of the pathological diagnosis information to the data on the observation image.

DETAILED DESCRIPTION

Described hereinafter by reference to the appended drawings are modes for implementation of the present disclosure (hereinafter, referred to as "embodiments").

First Embodiment

Figure 1:
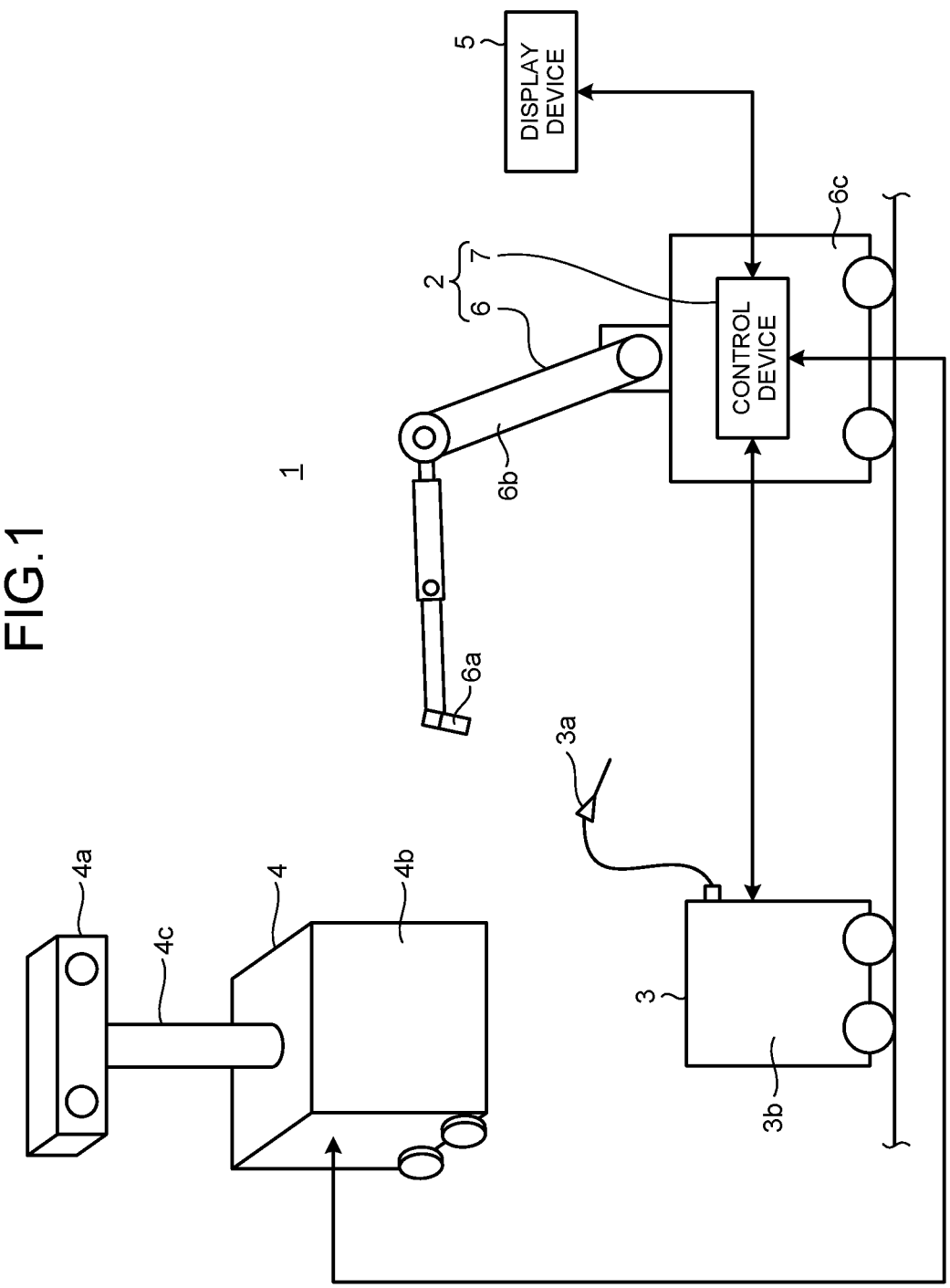
FIG. 1 is a diagram schematically illustrating a medical observation system according to a first embodiment.

FIG. 1 is a diagram schematically illustrating a medical observation system according to a first embodiment. A medical observation system 1 illustrated in FIG. 1 includes a medical observation device 2, a pathological diagnosis device 3, a position measurement device 4, and a display device 5. The medical observation device 2 is a surgical microscope and includes: a microscope device serving as an imaging device; and a control device 7 serving as a medical image processing device.

Described next is a configuration of the external appearance of the microscope device 6. The microscope device 6 has: a microscope unit 6a that magnifies the microstructure of a subject and captures an image of the magnified microstructure; a support unit 6b that supports the microscope unit 6a; and a base unit 6c that holds a proximal end of the support unit 6b and has the control device 7 built therein.

The microscope unit 6a has a tubular portion that is cylindrical. An aperture plane of a lower end portion of a main body portion of the microscope unit 6a is provided with a cover glass (not illustrated in the drawings). The tubular portion is able to be grasped by a user and has a size allowing the user to move the tubular portion while grasping the tubular portion when the user changes the imaging field of the microscope unit 6a. The shape of the tubular portion is not necessarily cylindrical and may be polygonally tubular.

The support unit 6b has plural arms and adjacent ones of these arms are turnably connected to each other via joint portions. A hollow part formed inside the support unit 6b has therethrough: a transmission cable that transmits various signals between the microscope unit 6a and the control device 7; and a light guide that transmits illumination light generated by the control device 7 to the microscope unit 6a.

The pathological diagnosis device 3 is a device that acquires images for pathological diagnosis. The pathological diagnosis device 3 has: a camera unit 3a that captures an image of a subject; and a base unit 3b having, built therein, a device that acquires data on the image captured by the camera unit 3a and performs pathological diagnosis thereon.

The position measurement device 4 is a device that measures three-dimensional positions of the microscope unit 6a and the camera unit 3a. The position measurement device 4 has: an infrared camera unit 4a that captures images of infrared light emitted from the microscope unit 6a and the camera unit 3a; a base unit 4b that has, built therein, a device that measures a three-dimensional position of each of the microscope unit 6a and the camera unit 3a, based on the infrared light captured by the infrared camera unit 4a; and a connection portion 4c that connects the infrared camera unit 4a and the base unit 4b to each other and is provided with a transmission cable.

Figure 2:
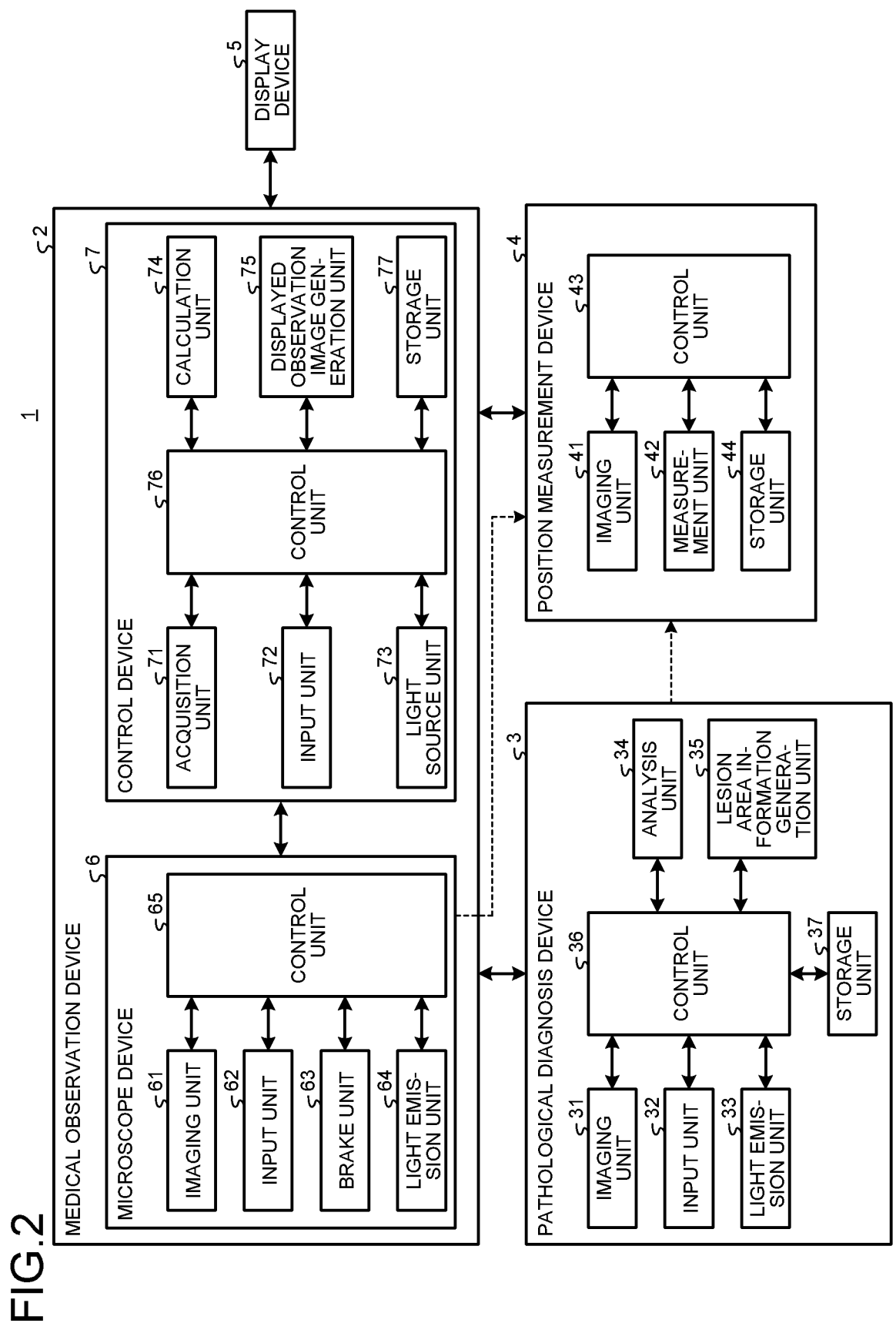
FIG. 2 is a block diagram illustrating a functional configuration of the medical observation system according to the first embodiment.

FIG. 2 is a block diagram illustrating a functional configuration of the medical observation system 1. Functional configurations of the medical observation device 2, the pathological diagnosis device 3, the position measurement device 4, and the display device 5 will be described by reference to FIG. 2.

Microscope Device 6

The microscope device 6 has an imaging unit 61, an input unit 62, a brake unit 63, a light emission unit 64, and a control unit 65.

The imaging unit 61 has: an optical system having focusing and zooming functions; and an imaging element that generates an image signal by receiving and photoelectrically converting an image of a subject, the image having been formed by the optical system. The optical system and the imaging element are provided inside the tubular portion of the microscope unit 6a. The imaging element is configured by use of an image sensor, such as a charge coupled device (CCD) or a complementary metal oxide semiconductor (CMOS). A signal including data on an observation image generated by the imaging unit 61 is transmitted to the control device 7 via the transmission cable. The imaging unit 61 may have two imaging elements provided with a predetermined parallax in their fields of view and may generate data on a three-dimensional observation image.

The input unit 62 receives input of an operation signal for the imaging unit 61 and an operation signal for the brake unit 63. The input unit 62 is provided at a position on a side surface of the tubular portion of the microscope unit 6a, the position being able to be operated in a state where a user has grasped the microscope unit 6a. The input unit 62 may be configured by further use of a foot switch that is able to be operated by a foot of the user.

The brake unit 63 has plural electromagnetic brakes respectively provided in the plural joint portions that the support unit 6b has. The electromagnetic brakes are released when the input unit 62 receives input of an instruction for release thereof. When an electromagnetic brake is released, turning of one of two arms that have been restricted in motion by that electromagnetic brake is enabled relative to the other one of the two arms. An actuator that assists in motion of an arm may be provided further at a joint portion.

The light emission unit 64 is fixed to a predetermined position on a side surface of the microscope unit 6a and is configured by use of three light emitting diodes (LEDs) that each emit infrared light. The infrared light emitted by the light emission unit 64 is used when the position measurement device 4 measures a three-dimensional position of the microscope device 6. A broken-lined arrow illustrated in FIG. 2 schematically illustrates the infrared light emitted by the light emission unit 64.

The control unit 65 controls operation of the microscope device 6, in cooperation with a control unit 76 of the control device 7. The control unit 65 is configured by use of at least one processor, such as a central processing unit (CPU), a field programmable gate array (FPGA), or an application specific integrated circuit (ASIC).

Control Device 7

The control device 7 includes an acquisition unit 71, an input unit 72, a light source unit 73, a calculation unit 74, a displayed observation image generation unit 75, the control unit 76, and a storage unit 77. The control device 7 has functions of the medical image processing device according to the first embodiment.

The acquisition unit 71 acquires image data captured by the microscope device 6 and transmitted through the transmission cable. The image data also include information related to imaging, such as focus position, zooming, exposure time, and imaging time, in the imaging.

The input unit 72 receives input of various types of information including an instruction signal for changing brightness level of an image. The input unit 72 is configured by use of a user interface, such as a keyboard, a mouse, a touch panel, and/or a foot switch. The input unit 72 may also have at least a part of functions of the input unit 62 of the microscope device 6.

The light source unit 73 generates illumination light to be supplied to the microscope device 6 via the light guide. The light source unit 73 is configured by use of: a discharge lamp, such as a xenon lamp or a metal halide lamp; a solid state light emitting element, such as a light emitting diode (LED) or a laser diode (LD); or a light emitting member, such as a laser light source or a halogen lamp.

By using: data on an observation image of a subject and magnification information in imaging thereof, the observation image having been generated by the microscope device 6; data on a lesion area image depicting a boundary of a lesion area of the subject and magnification information in imaging thereof, the data having been generated by the pathological diagnosis device 3; and positional information on the microscope device 6 and positional information on the pathological diagnosis device 3, the positional information having been measured by the position measurement device 4; the calculation unit 74 calculates relative information including a relative position and a relative magnification of the lesion area with respect to the observation image.

Based on the relative information calculated by the calculation unit 74, the displayed observation image generation unit 75 generates data on a displayed observation image, by converting position, shape, and size of the lesion area image into position, shape, and size that will be suitable in the observation image and superimposing the converted lesion area image on the observation image.

The control unit 76 controls operation of the control device 7, and centrally controls, in cooperation with the control unit 65 of the microscope device 6, operation of the medical observation device 2. The control unit 76 is configured, together with the calculation unit 74 and the displayed observation image generation unit 75, by use of one or plural processors selected from a group including: CPUs; FPGAs; and ASICs.

The storage unit 77 stores therein various programs including a medical image processing program executed by the control device 7 and temporarily stores therein data being arithmetically processed by the control device 7. The storage unit 77 is configured by use of a read only memory (ROM) and/or a random access memory (RAM). The medical image processing program may be widely distributed by being recorded in a computer readable recording medium, such as a hard disk, a flash memory, a CD-ROM, a DVD-ROM, or a flexible disk.

Pathological Diagnosis Device 3

The pathological diagnosis device 3 includes an imaging unit 31, an input unit 32, a light emission unit 33, an analysis unit 34, a lesion area information generation unit 35, a control unit 36, and a storage unit 37.

The imaging unit 31 has: an optical system having focusing and zooming functions; and an imaging element configured by use of an image sensor, such as a CCD or a CMOS. The imaging unit 31 is provided inside the camera unit 3a.

The input unit 32 receives input of an operation signal for the imaging unit 31.

The light emission unit 33 is: configured by use of three LEDs that each emit infrared light; and fixed to a predetermined position in the camera unit 3a. The infrared light emitted by the light emission unit 33 is used when the position measurement device 4 measures a three-dimensional position of the pathological diagnosis device 3.

The analysis unit 34 identifies a lesion by performing pathological diagnosis based on data on a pathological observation image generated by the imaging unit 31.

The lesion area information generation unit 35 generates, based on a result of the analysis by the analysis unit 34, lesion area information related to a lesion area, the lesion area information being data on a lesion area image depicting the shape and range of the lesion area.

The control unit 36 controls operation of the pathological diagnosis device 3. The control unit 36 is configured, together with the analysis unit 34 and the lesion area information generation unit 35, by use of one or plural processors selected from a group including: CPUs; FPGAs; and ASICs.

The storage unit 37 stores therein various programs executed by the pathological diagnosis device 3 and temporarily stores therein data that are being arithmetically processed by the pathological diagnosis device 3. The storage unit 37 is configured by use of a ROM and/or a RAM.

Position Measurement Device 4

The position measurement device 4 includes an imaging unit 41, a measurement unit 42, a control unit 43, and a storage unit 44.

The imaging unit 41 is configured by use of an image sensor, such as a CCD or a CMOS, detects infrared light emitted by the light emission unit 64 of the microscope device 6, and captures an image of the infrared light emitted by the light emission unit 33 of the pathological diagnosis device 3. The imaging unit 41 is provided inside the infrared camera unit 4a.

The measurement unit 42 measures a three-dimensional position of the microscope unit 6a of the microscope device 6 by using the infrared light acquired by the imaging unit 41, and measures a three-dimensional position of the camera unit 3a of the pathological diagnosis device 3.

The control unit 43 controls operation of the position measurement device 4. The control unit 43 is configured, together with the measurement unit 42, by use of one or plural processors selected from a group including: CPUs, FPGAs, and ASICs.

The storage unit 44 stores therein various programs executed by the position measurement device 4 and temporarily stores therein data being arithmetically processed by the position measurement device 4. The storage unit 44 is configured by use of a ROM and/or a RAM.

Display Device 5

The display device 5 receives an image signal for display generated by the control device 7 and displays an image corresponding to the image signal. The display device 5 has a display panel formed of liquid crystal or organic electroluminescence (EL).

Figure 3:
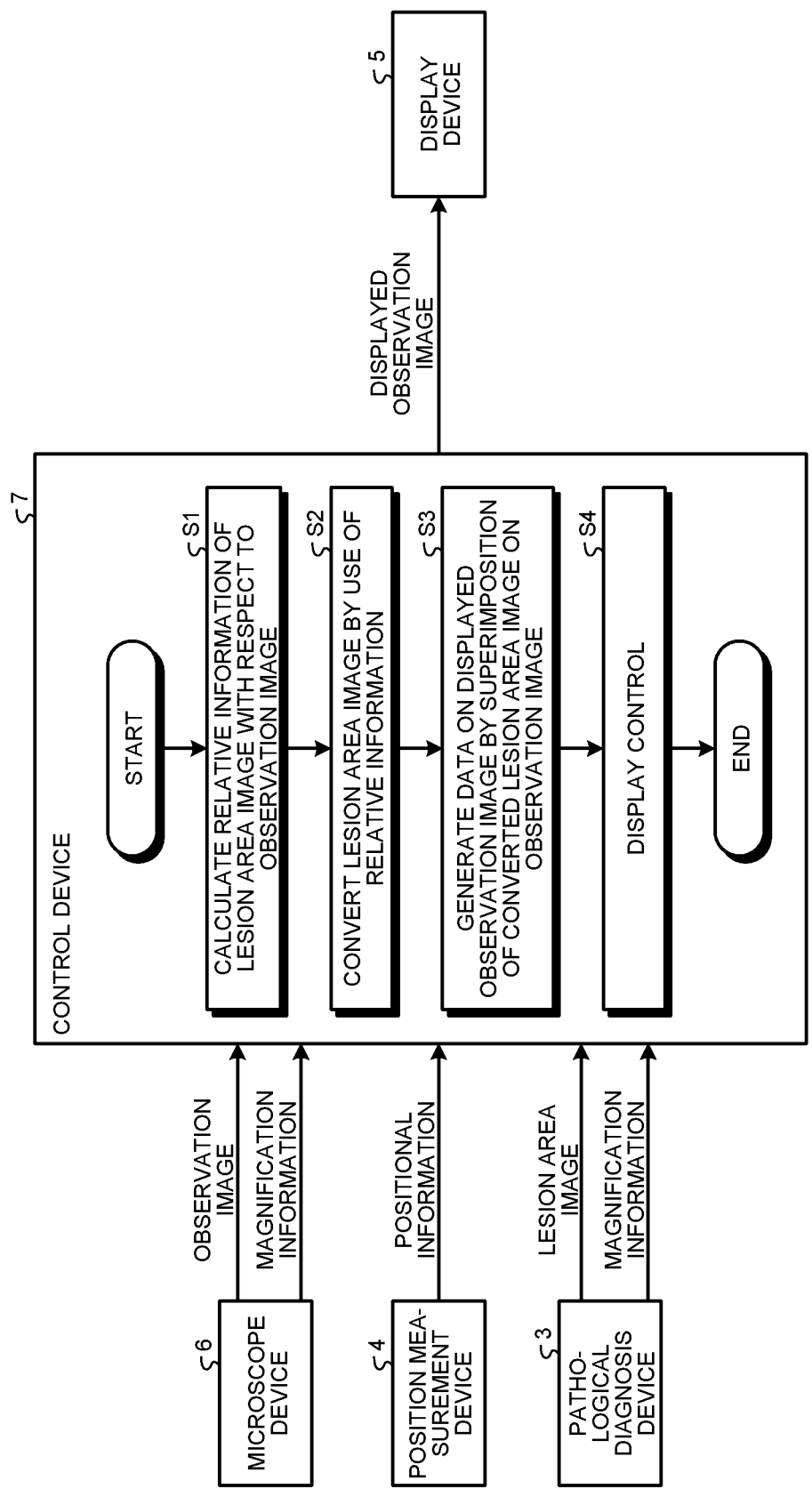
FIG. 3 is a flow chart illustrating an outline of processing performed by a medical image processing device according to the first embodiment.

FIG. 3 is a flow chart illustrating an outline of processing performed by the control device 7.

Firstly, the calculation unit 74 calculates relative information on a lesion area image with respect to an observation image acquired from the microscope device 6 by using: data and magnification information on the observation image; data and magnification information on a lesion area image acquired from the pathological diagnosis device 3; and positional information on the microscope device 6 and positional information on the pathological diagnosis device 3 that have each been acquired from the position measurement device 4 (Step S1). Through this processing by the calculation unit 74, calculation for conversion of the original lesion area image into a lesion area image as viewed in the observation image is found.

Figure 4:
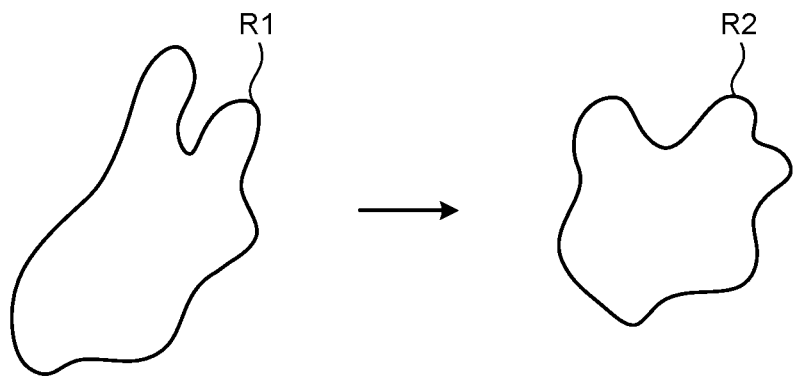
FIG. 4 is a diagram illustrating lesion area images before and after conversion.

Subsequently, the displayed observation image generation unit 75 converts the lesion area image by using the relative information calculated by the calculation unit 74 (Step S2). Through this conversion, as illustrated in FIG. 4, in the lesion area image, a lesion area R1 generated by the lesion area information generation unit 35 is modified into a lesion area R2 corresponding to a shape as viewed in the field of the observation image.

The displayed observation image generation unit 75 thereafter generates data on a displayed observation image by positioning and superimposing data on the converted lesion area image, on the data on the observation image (Step S3).

Figure 5:
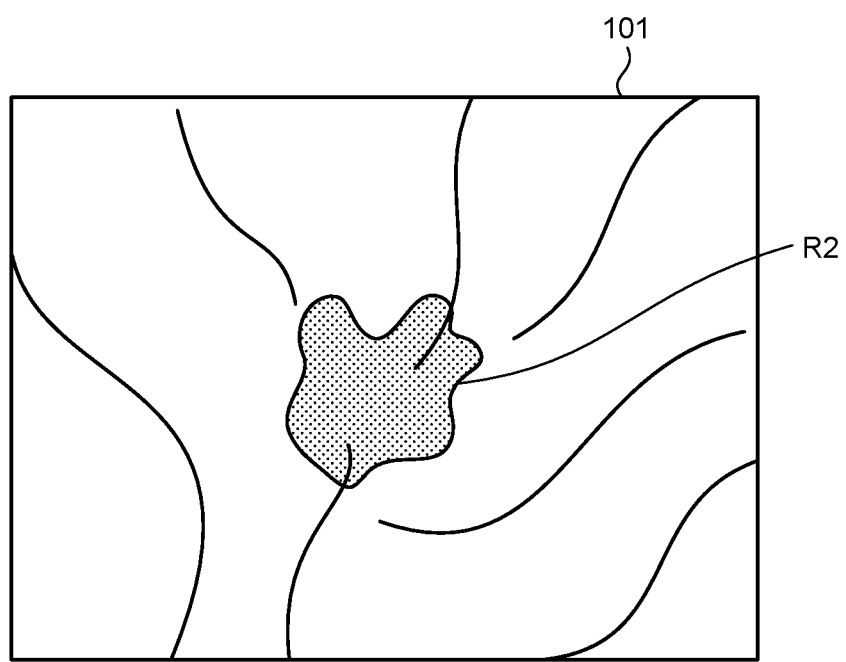
FIG. 5 is a diagram illustrating a display example of a displayed observation image displayed by a display device, according to the first embodiment.

Subsequently, the control unit 76 performs control of outputting the data on the displayed observation image to the display device 5 and causing the display device 5 to display the displayed observation image (Step S4). FIG. 5 is a diagram illustrating a display example of the displayed observation image displayed by the display device 5. A displayed observation image 101 illustrated in FIG. 5 has been displayed with a lesion area superimposed thereon.

According to the above described first embodiment, a doctor is able to easily identify the position and area of a lesion in an observation image during surgery because: a lesion area image generated by a pathological diagnosis device is converted based on relative information calculated by use of data and magnification information on the observation image, data and magnification information on the lesion area image, and positional information on a microscope device and positional information on the pathological diagnosis device that have each been measured by a position measurement device; and data on a displayed observation image are generated by superimposition of the converted lesion area image on the observation image.

Furthermore, according to the first embodiment, a result of pathological diagnosis is displayed as a single image by positioning the result on an observation image captured by a video microscope for surgery, and a more accurate removal range is thereby able to be determined and improvement in surgical results including improvement in the extirpation rate and reduction in the complication rate is thereby expected. Moreover, surgery is able to be accomplished by use of just a single observation image, and improvement in surgical efficiency, that is, decrease in the surgical time, is expected.

Furthermore, according to the first embodiment, pathological diagnosis at the cellular level is performed in real time in situ without sampling of a specimen during surgery, and thus the surgical time is able to be decreased with minimal invasivity.

Second Embodiment

A medical observation system according to a second embodiment has a configuration that is similar to that of the above described medical observation system 1 according to the first embodiment. Hereinafter, components of the medical observation system according to the second embodiment will be assigned with reference signs that are the same as those of the corresponding components of the medical observation system 1.

According to the second embodiment, a lesion area information generation unit 35 of a pathological diagnosis device 3 generates numerical data, such as coordinate values indicating the position of a lesion area, and outputs the numerical data as lesion area information to a control device 7; and the control device 7 generates data on a displayed observation image by performing image processing on the lesion area, which has been identified in an observation image based on the numerical data, the image processing being different from that on the other area.

Figure 6:
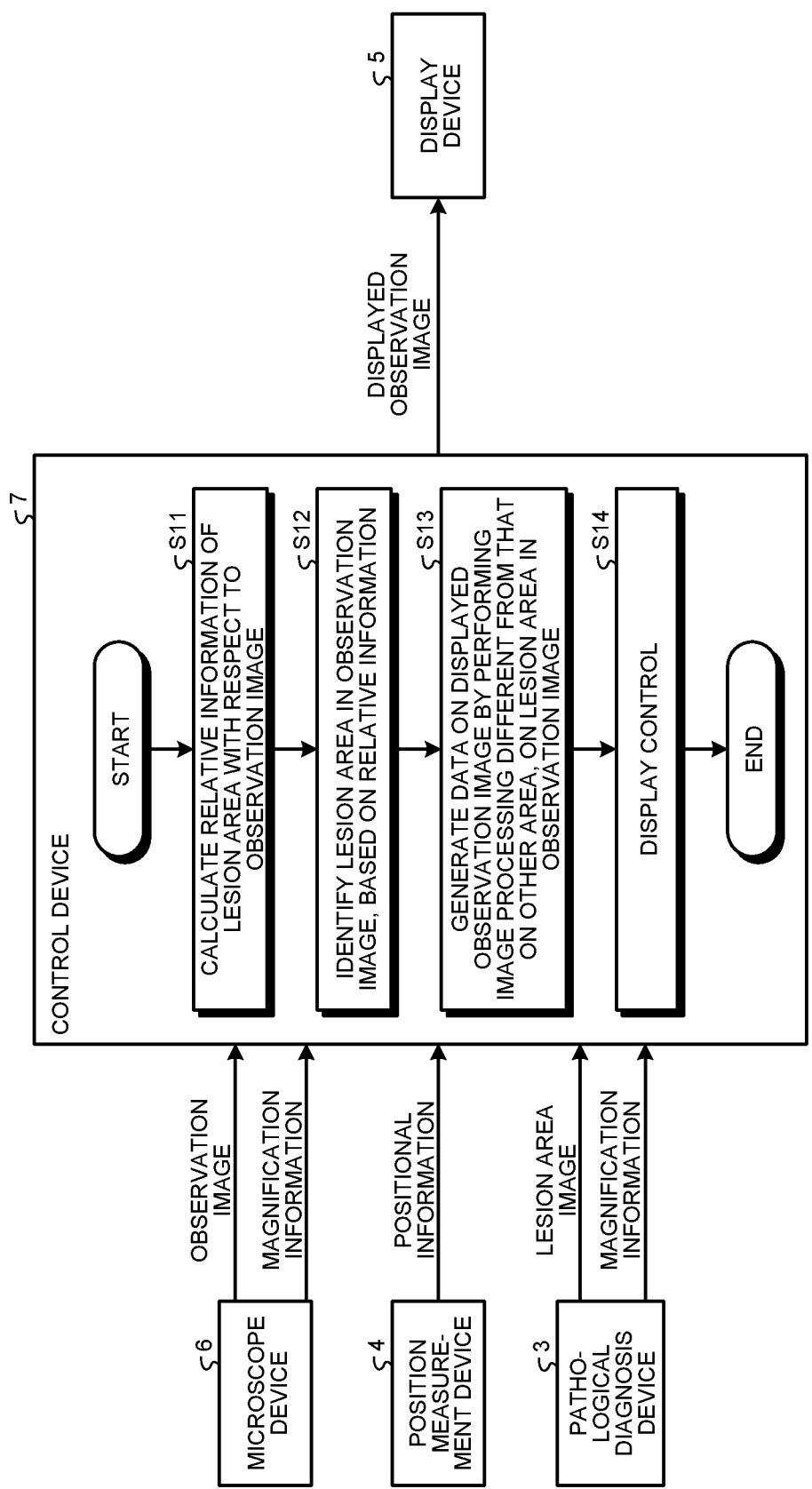
FIG. 6 is a flow chart illustrating an outline of processing performed by a medical image processing device according to a second embodiment.

FIG. 6 is a flow chart illustrating an outline of processing performed by the control device 7 according to the second embodiment. Firstly, a calculation unit 74 calculates relative information on a lesion area image with respect to an observation image acquired from a microscope device 6 by using: data and magnification information on the observation image; lesion area information and magnification information acquired from the pathological diagnosis device 3; and positional information on the microscope device 6 and positional information on the pathological diagnosis device 3 that have each been acquired from a position measurement device 4 (Step S11).

Subsequently, a displayed observation image generation unit 75 converts the lesion area information, based on the relative information calculated by the calculation unit 74, and identifies a lesion area in the observation image (Step S12).

The displayed observation image generation unit 75 thereafter generates data on a displayed observation image by performing image processing on the identified lesion area, the image processing being different from that on the other area (Step S13). For example, the displayed observation image generation unit 75 generates data on a displayed observation image to be displayed with a lesion area being emphasized therein, by changing image quality parameters, such as contrast and brightness, in a part corresponding to the lesion area. Visibility of the lesion area in the displayed observation image generated thereby is able to be improved.

Subsequently, a control unit 76 performs control of outputting the data on the displayed observation image to a display device 5 and causing the display device 5 to display the displayed observation image (Step S14).

According to the second embodiment, the displayed observation image generation unit 75 may generate data on a lesion area image by using numerical data acquired from the pathological diagnosis device 3, and may generate data on a displayed observation image by superimposing the lesion area image further on an observation image.

According to the above described second embodiment, similarly to the first embodiment, a doctor is able to easily identify the position and area of a lesion in an observation image during operation because: a lesion area in an observation image is identified based on relative information on the lesion area image with respect to the observation image, the relative information having been calculated by use of data and magnification information on the observation image, lesion area information and magnification information generated by a pathological diagnosis device, and positional information on a microscope device and positional information on the pathological diagnosis device that have each been measured by a position measurement device; and data on the displayed observation image are generated by image processing on the identified lesion area, the image processing being different from that on the other area.

Furthermore, according to the second embodiment, since image processing on a lesion area is just made different from that on the other area, the overall device configuration is able to be simplified.

Third Embodiment

Figure 7:
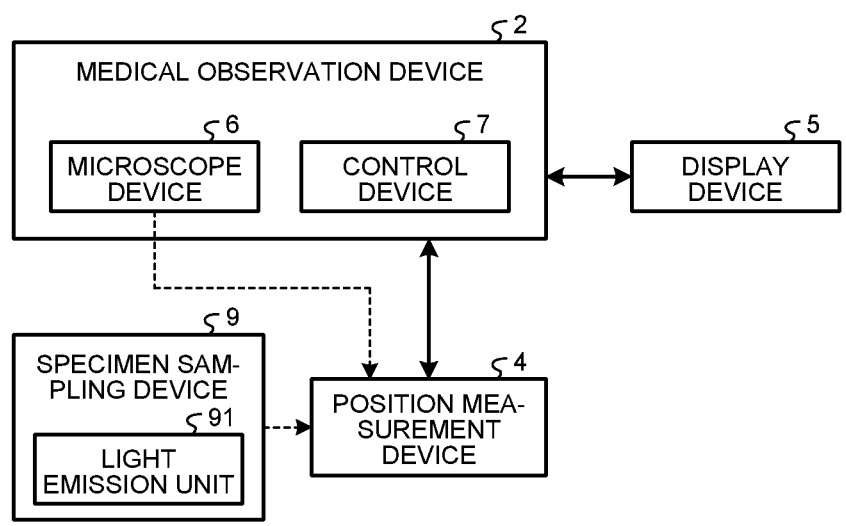
FIG. 7 is a block diagram illustrating a functional configuration of a medical observation system according to a third embodiment.

FIG. 7 is a block diagram illustrating a functional configuration of a medical observation system according to a third embodiment. A medical observation system 8 illustrated in FIG. 7 includes a medical observation device 2, a position measurement device 4, a display device 5, and a specimen sampling device 9.

The specimen sampling device 9 is a device that samples a specimen from a subject, for pathological diagnosis. The specimen sampling device 9 has a surgical tool for sampling a specimen. A light emission unit 91 that emits infrared light for position detection is provided at a predetermined position in the surgical tool. The light emission unit 91 has three LEDs, similarly to the light emission unit 64 described above.

The specimen sampled by the specimen sampling device 9 is transferred to a pathological room and thereafter subjected to pathological diagnosis by a doctor in charge. A result of the pathological diagnosis is sent to a surgical room and an input unit 72 of a control device 7 therein receives input thereof. Examples of the result of the pathological diagnosis include a result having lesion areas in the specimen that have been classified by grade.

Figure 8:
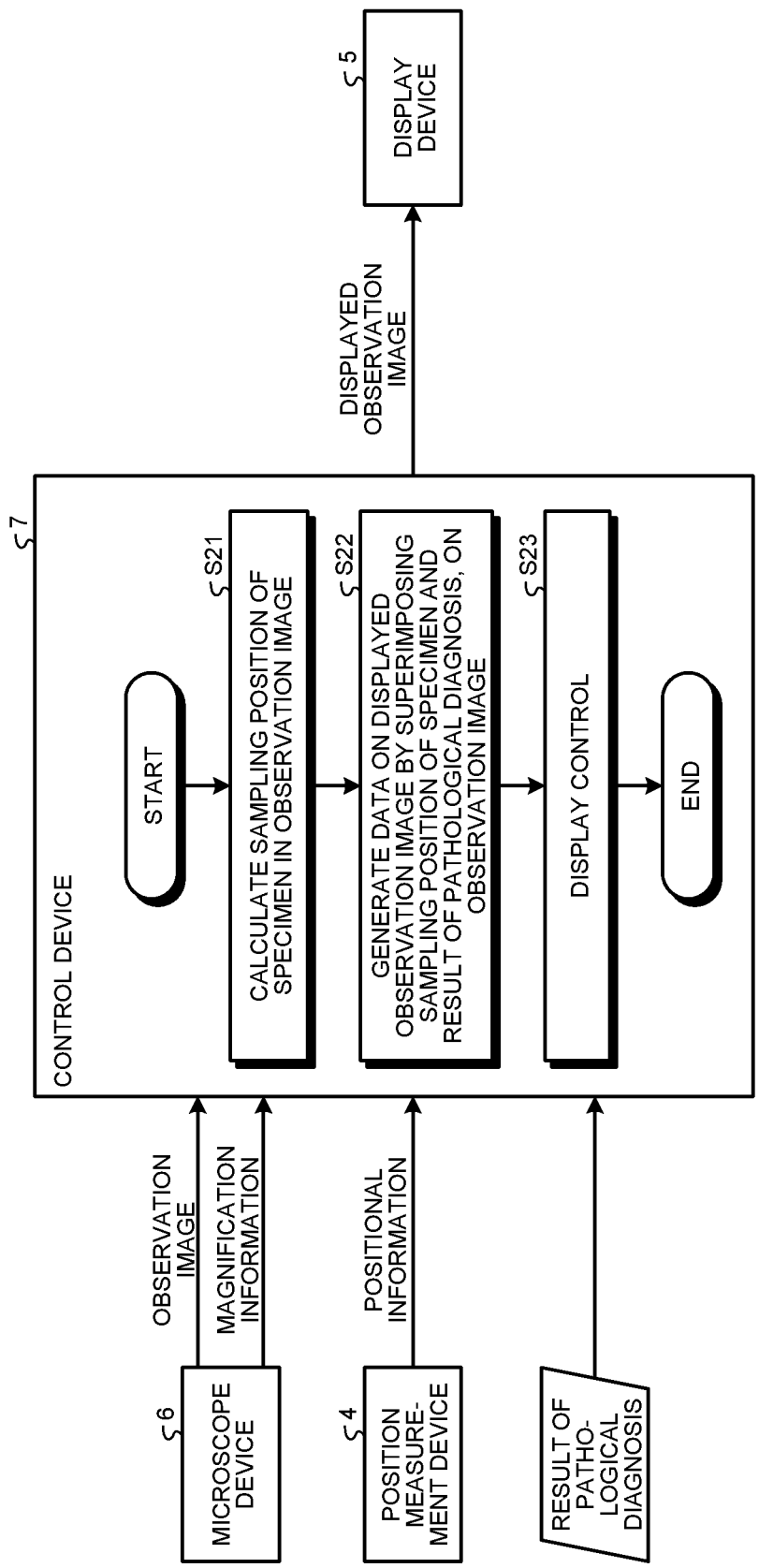
FIG. 8 is a flow chart illustrating an outline of processing performed by a medical image processing device according to the third embodiment.

FIG. 8 is a flow chart illustrating an outline of processing performed by the control device 7 according to the third embodiment. Firstly, a calculation unit 74 calculates a sampling position of a specimen from a subject, the sampling position being a pathologically diagnosed position in an observation image acquired from a microscope device 6, by using data and magnification information on the observation image, and positional information on the microscope device 6 and positional information on the specimen sampling device 9 that have each been acquired from the position measurement device 4 (Step S21).

Subsequently, the displayed observation image generation unit 75 generates data on a displayed observation image by superimposing information and a pathological diagnosis result on the observation image, the information indicating the sampling position of the specimen in the observation image calculated by the calculation unit 74, the pathological diagnosis result having been received by the input unit 72 (Step S22).

Figure 9:
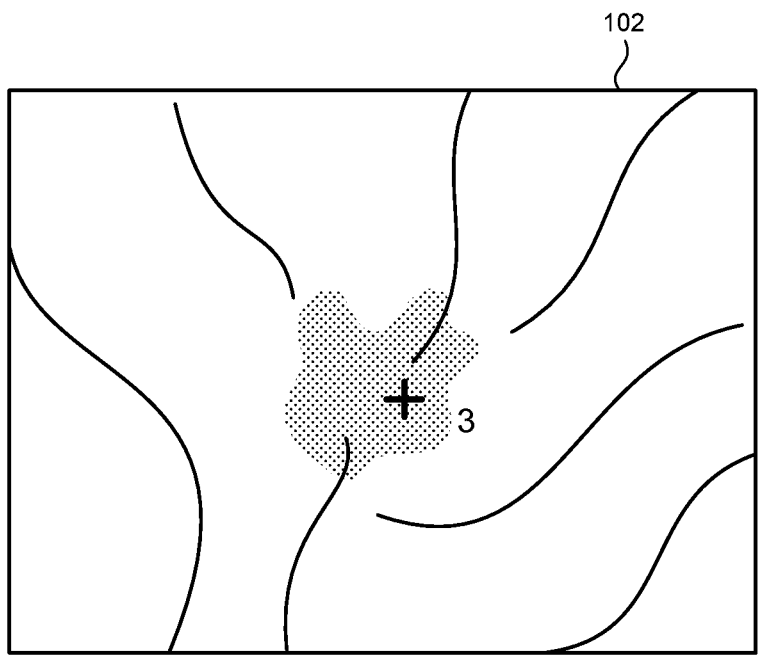
FIG. 9 is a diagram illustrating a display example of a displayed observation image displayed by a display device, according to the third embodiment.

Subsequently, a control unit 76 performs control of outputting the data on the displayed observation image to the display device 5 and causing the display device 5 to display the displayed observation image (Step S23). FIG. 9 is a diagram illustrating a display example of the displayed observation image displayed by the display device 5. A displayed observation image 102 illustrated in FIG. 9 has the sampling position of the specimen displayed with the mark, "+", and the diagnosis result displayed with the grade number, "3".

According to the above described third embodiment, a result of pathological diagnosis and a sampling position of a specimen sampled by a specimen sampling device that samples the specimen from a subject are superimposed on data on an observation image by use of pathological diagnosis information including the result of pathological diagnosis; data on a displayed observation image are thereby generated; and thus similarly to the first embodiment, a doctor is able to easily identify the position and area of a lesion in the observation image during operation, the pathological diagnosis using the specimen.

Furthermore, according to the third embodiment, in a known pathological diagnosis environment also, a pathological diagnosis result is able to be referred to in the field of a microscope, and accurate determination of a resection line is enabled.

Other Embodiments

Figure 10:
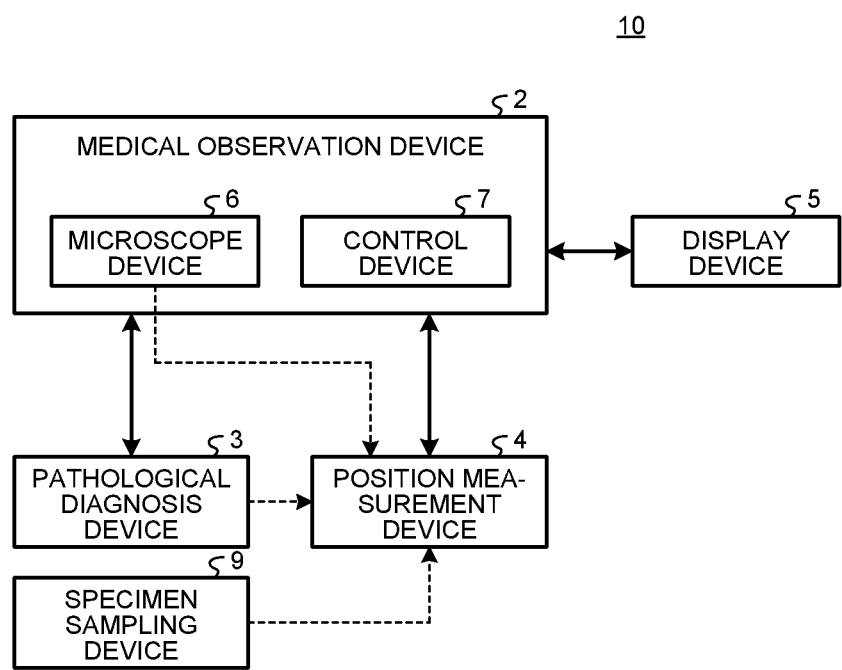
FIG. 10 is a block diagram illustrating a functional configuration of a medical observation system according to another embodiment.

Embodiments for implementation have been described thus far, but the present disclosure is not to be limited only to the above described first to third embodiments. For example, like a medical observation system 10 illustrated in a block diagram of FIG. 10, the third embodiment may be added to the first or second embodiment, and data on a displayed observation image may be generated by superimposition of lesion area information and a diagnosis result for a pathological specimen that have been generated by the pathological diagnosis device 3 on an observation image generated by the microscope device 6.

Furthermore, at least one of functions of the analysis unit 34 and lesion area information generation unit 35 of the pathological diagnosis device 3 may be included in the control device 7.

Furthermore, instead of using the above described optical three-dimensional measurement method, the position measurement device may use a magnetic three-dimensional measurement method. A navigation system for surgery may be used therefor.

Furthermore, an encoder may be installed at a joint portion between arms of the support unit 6b of the microscope device 6 and a three-dimensional position of the microscope unit 6a may be measured based on angle information between the adjacent arms. If the camera unit 3a of the pathological diagnosis device 3 is configured to be supported by a support unit having plural arms, a three-dimensional position of the camera unit 3a is able to be measured by installation of an encoder at a joint portion between arms, similarly to the microscope device 6. According to such a configuration, a position measurement device does not need to be provided separately and space is able to be saved.

Furthermore, if the microscope device 6 has a function of generating three-dimensional image data, a position of the pathological diagnosis device 3 or specimen sampling device 9 may be measured by use of the three-dimensional image data. In this case also, a position measurement device does not need to be provided separately and space is thus able to be saved.

Furthermore, the medical observation device may be a medical endoscope that is inserted into a subject and captures images of the interior of the subject.

Furthermore, among the photodynamic diagnosis devices described in Japanese Laid-open Patent Publication No. 2016-202726, the fluorescence imaging device may be used as the pathological diagnosis device.

According to the present disclosure, a doctor is able to easily identify the position and area of a lesion in an observation image during surgery.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising circuitry configured to:
    calculate relative information including relative positional relation of a lesion area in an observation image of a subject captured by an imager to a pathologically diagnosed lesion area of the subject acquired by a pathological diagnosis imager, by using data and magnification information on the observation image on the subject and data and magnification information on a pathologically diagnosed lesion area image depicting the pathologically diagnosed lesion area of the subject on pathological diagnosis information on the subject, and positional information regarding a position of the imager and a position of the pathological diagnosis imager; and
    generate, based on the relative information, data on a displayed observation image resulting from addition of the pathological diagnosis information to the data on the observation image.

2. The medical image processing device according to claim 1, wherein the circuitry is configured to:
    convert the pathologically diagnosed lesion area image, based on the relative information; and
    generate the data on the displayed observation image by superimposing the converted pathologically diagnosed lesion area image on the observation image.

3. The medical image processing device according to claim 1, wherein the circuitry is configured to:
    identify, based on the relative information, the lesion area in the observation image; and
    generate the data on the displayed observation image performing image processing on the identified lesion area, the image processing being different from that on an area other than the identified lesion area.

4. The medical image processing device according to claim 3, wherein the circuitry is configured to:
    generate data on the pathologically diagnosed lesion area image depicting a boundary of the lesion area; and
    superimpose the lesion area image on the observation image when the data on the displayed observation image is generated.

5. The medical image processing device according to claim 1, wherein
    the pathological diagnosis information includes a result of pathological diagnosis using a specimen sampled by a specimen sampling device that samples the specimen from the subject,
    the pathologically diagnosed position is a sampling position of the specimen, and
    the circuitry is configured to superimpose the sampling position of the specimen and the result of pathological diagnosis on the data on the observation image when the data on the displayed observation image is generated.

6. A medical observation system, comprising:
an imager configured to generate data on an observation image of a subject; and
circuitry configured to:
calculate relative information including relative positional relation of a lesion area in the observation image to a pathologically diagnosed lesion area of the subject acquired by a pathological diagnosis imager, by using data and magnification information on the observation image on the subject and data and magnification information on a pathologically diagnosed lesion area image depicting the pathologically diagnosed lesion area of the subject on pathological diagnosis information on the subject, and positional information regarding a position of the imager and a position of the pathological diagnosis imager; and
generate, based on the relative information, data on a displayed observation image resulting from addition of the pathological diagnosis information to the data on the observation image.

7. The medical observation system according to claim 6, further comprising a position sensor configured to measure a three-dimensional position of the imager.

8. The medical observation system according to claim 7, further comprising a pathological diagnosis device including:
an analyzer configured to perform pathological diagnosis by analyzing the image data from the pathological diagnosis imager.

9. An operation method in a medical image processing device, the operation method comprising:
calculating, by using data on an observation image of a subject captured by an imager and pathological diagnosis information on the subject, relative information including relative positional relation of a position of a pathologically diagnosed lesion area acquired by a pathological diagnosis imager in the subject with respect to a lesion area in the observation image; data and magnification information on the observation image; data and magnification information on a pathologically diagnosed lesion area image depicting the pathologically diagnosed lesion area of the subject; and positional information regarding a position of the imager and a position of the pathological diagnosis imager; and
generating, based on the relative information, data on a displayed observation image resulting from addition of the pathological diagnosis information to the data on the observation image.

10. A non-transitory computer readable recording medium on which an executable program for medical image processing, the program instructing a processor of a computer to execute:
calculating, by using data on an observation image of a subject captured by an imager and pathological diagnosis information on the subject, relative information including relative positional relation of a position of a pathologically diagnosed lesion area acquired by a pathological diagnosis imager in the subject with respect to a lesion area in the observation image; data and magnification information on the observation image; data and magnification information on a pathologically diagnosed lesion area image depicting the pathologically diagnosed lesion area of the subject; and positional information regarding a position of the imager and a position of the pathological diagnosis imager; and
generating, based on the relative information, data on a displayed observation image resulting from addition of the pathological diagnosis information to the data on the observation image.

11. The non-transitory computer readable recording medium according to claim 10, wherein the program instructing a processor of a computer to execute:
converting the pathologically diagnosed lesion area image, based on the relative information; and
generating the data on the displayed observation image by superimposing the converted pathologically diagnosed lesion area image on the observation image.

12. The operation method according to claim 9, further comprising:
converting the pathologically diagnosed lesion area image, based on the relative information; and
generating the data on the displayed observation image by superimposing the converted pathologically diagnosed lesion area image on the observation image.

* * * * *